United States Patent [19]

Horodysky et al.

[11] 4,375,419

[45] Mar. 1, 1983

[54] NITROGEN-CONTAINING PRODUCTS OF PHOSPHOSULFURIZED AMIDES AND LUBRICANTS CONTAINING SAME

[75] Inventors: Andrew G. Horodysky, Cherry Hill; Joan M. Kaminski, Clementon, both of N.J.

[73] Assignee: Mobil Oil Corporation, New York, N.Y.

[21] Appl. No.: 263,535

[22] Filed: May 14, 1981

[51] Int. Cl.$^3$ .................. C10M 1/20; C10M 1/32; C10M 1/44; C07G 17/00
[52] U.S. Cl. .................. 252/46.7; 252/389 A; 260/132
[58] Field of Search .................. 252/46.7, 389 A; 260/132

[56] References Cited

U.S. PATENT DOCUMENTS 2,393,934  1/1946  Reiff et al. .................. 252/46.7
2,614,075  10/1952  Bartleson .................. 252/46.7 X

*Primary Examiner*—W. J. Shine
*Attorney, Agent, or Firm*—Charles A. Huggett; Michael G. Gilman; Claude E. Setliff

[57] ABSTRACT

The invention herein is concerned with new compositions of matter made by (1) reacting phosphorus pentasulfide with an amide and (2) reacting this product with a nitrogen-containing compound, and lubricant compositions containing same. The compositions reduce friction to a greater extent than lubricants containing no additive and, when placed in lubricating oils and used in an internal combustion engine, fuel consumption is reduced.

23 Claims, No Drawings

NITROGEN-CONTAINING PRODUCTS OF PHOSPHOSULFURIZED AMIDES AND LUBRICANTS CONTAINING SAME

BACKGROUND OF THE INVENTION

1. Field of the Invention

The invention is concerned with a novel group of compounds and their use as friction reducing and antiwear additives in lubricants, i.e. lubricant compositions containing same.

2. Description of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present therein.

Friction is also a problem any time two surfaces are in sliding or rubbing contact. It is of especial significance in an internal combustion engine, because loss of a substantial amount of the theoretical mileage possible from a gallon of fuel is traceable directly to friction.

Phosphorus compounds are known to be useful as additives to lubricants to improve some property thereof, e.g. the antiwear property. Further, lubricants containing metal salts of phosphorus acids are also known. However, no prior art is known disclosing or suggesting the reaction product of the present invention, as a multifunctional anti-wear, anti-oxidant, friction-reducing additive.

SUMMARY OF THE INVENTION

In accordance with the invention, there is provided a reaction product made by (1) reacting a phosphorus polysulfide, such as phosphorus pentasulfide, with a hydroxy aliphatic hydrocarbylamide of the formula

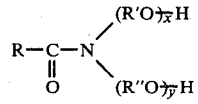

wherein R is an hydrocarbyl group containing 6 to 30 carbon atoms, R' and R" are aliphatic groups containing 1 to 6 carbon atoms and x and y are 1 to 7, followed by (2) reacting this product with a nitrogen-containing compound. In the above formula x and y are preferably equal to 1. Further, R can be alkyl, alkenyl, cycloalkyl, cycloalkenyl, aralkyl, alkaryl and the like, and R' and R" can each be methyl ethyl, propyl, isopropyl, butyl, secondary butyl, isobutyl, pentyl, isomeric pentyl and hexyl. R' and R" is each preferably ethyl.

The invention also provides a lubricant composition comprising a major proportion of a lubricant and a friction reducing amount of the reaction product.

DESCRIPTION OF THE SPECIFIC EMBODIMENTS

The novel compounds of this invention are made by (1) reacting phosphorus polysulfide, such as phosphorus pentasulfide, with an amide having the formula set forth hereinabove and (2) reacting the resulting product with a nitrogen-containing compound. The product of the first reaction is a complex one and its structure is not known, although it may contain one or more of the following structures, illustrated with a bis-(2-hydroxyethyl) hydrocarbylamide wherein each R' and R" is chosen to be ethyl groups.

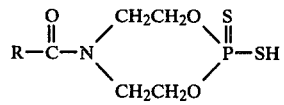

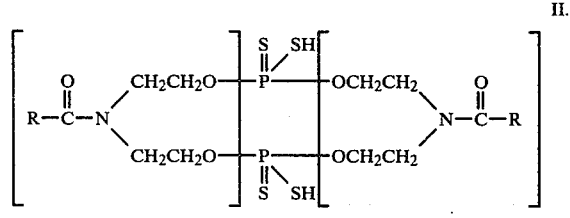

These 2 structures would require 2 moles of the amide and 1 mole of $P_2S_5$.

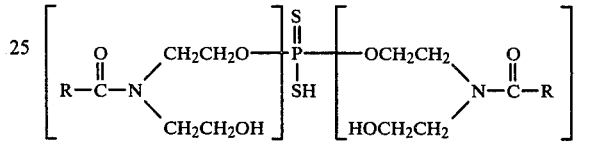

Other similar oligomers could also be formed in varying proportions.

Structure III would require 4 moles of amide per mole of $P_2S_5$. However, the amount of reactants in reaction (1) of the Summary is not limited to the stated ratios. It is contemplated that in that reaction, from about 12 moles to about 2 moles of amide, preferably from about 4 moles to about 2 moles, can be used per mole of $P_2S_5$. Preferably, a significant portion of hydroxyl groups available for reaction are phosphosulfurized. At least 5 to 10% of available hydroxyls must be phosphosulfurized to gain a benefit. However, up to equivalent amounts can be used, although phosphosulfurization of 30–75% is preferred.

The temperature of this reaction can be within the range of from about 50° C. to about 140° C., preferably from about 90° C. to about 110° C.

Reaction (2) can be carried out at from about 50° C. to about 120° C., preferably from about 80° C. to about 100° C. Stoichiometric amounts of reagents may be used, or, if desired, a slight excess of about 1 to 5%. By "stoichiometric amounts" is meant sufficient amount of nitrogen-containing compound to supply the required amount thereof to react with all the acid groups present in the complex product.

The nitrogen-containing compound can be any of a variety of compounds, including aliphatic or aromatic primary, secondary or tertiary amines. The aliphatic amines will contain from 6 to 30 carbon atoms and will preferably be alkyl, alkenyl, alkaryl, aralkyl, or cycloalkenyl amines having 12 to 20 carbon atoms. These include cyclohexylamine, hexylamine, octylamine, nonylamine, oleylamine, stearylamine, cocoamine, and the like, as well as the secondary amines such as dicyclohexylamines. Further included are primary, secondary and tertiary aliphatic, or aromatic diamines such as N-oleyl-1,3-propylenediamine, N-coco-1,3-propylenediamine, N-methyl-N-oleylamine, N-methyl- N-cocoamine, N,N-dimethyl-N-oleylamine and N,N-diamethyl-N-cocoamine and the like. Where aromatic amines are used, the aromatic portion will have from 6 to 14 carbon atoms. That is they will be either the phenyl, naphthyl or anthryl group.

While atmospheric pressure is generally preferred, either reaction can be advantageously run at from about 0.5 to about 2.0 atmospheres. Furthermore, where conditions warrant it, a solvent may be used. In general, reaction (1) can be run in the absence of solvent or in non-polar, unreactive solvent including benzene, toluene, xylene, heptane or 1,4-dioxane. Reaction (2) can be run in the absence of solvent or in any alcoholic solvent including isopropanol and n-butanol or in a mixture of polar and non-polar solvents, such as toluene and isopropanol. The times of reactions for the reactants are not critical. Thus, any phase of the process can be carried out in from 1 to 8 hours.

Most of the amides are commercially available or they may be made using known methods by reacting a bis(hydroxy aliphatic) amine with the appropriate aliphatic acid. For example, a preferred amide, bis-(2-hydroxyethyl) hydrocarbylamide, can be prepared by reacting diethanolamine with the appropriate hydrocarbyl carboxylic acid.

Of particular significance, in accordance with the present invention, is the ability to improve the friction properties of oleaginous materials such as lubricating media which may comprise either a mineral oil or a synthetic oil, or a grease therefrom. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800.

In instances where synthetic oils are desired in preference to mineral oils, or in combination therewith, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenol) ether, phenoxy phenylethers.

It is to be understood, however, that the compositions contemplated herein can also contain other materials. For example, corrosion inhibitors extreme pressure agents, viscosity index improvers, detergents, dispersants, co-antioxidants, anti-wear agents and the like can be used. These materials do not detract from the value of the compositions of this invention, but rather they serve to impart their customary properties to the particular compositions in which they are incorporated.

In general, the preformed adducts of the present invention may be employed in any amount which is effective for imparting the desired degree of friction reduction anti-corrosion or anti-wear activity. In many applications, however, the adduct is effectively employed in amounts from about 0.1% to about 10% by weight, and preferably from about 0.5 to about 5% of the total weight of the composition.

The following Examples will present illustrations of the invention. They are illustrative only, and are not meant to limit the invention. Parts are by weight.

EXAMPLE 1

N,N-(bis-2-hydroxyethyl)oleamide

Obtained commercially or made by reacting bis(2-hydroxyethyl)amine with oleic acid.

EXAMPLE 2

Phosphosulfurization of N,N-(bis-2-hydroxyethyl)oleamide

Approximately 400 parts of N,N-(bis-2-hydroxyethyl) oleamide (Etomid O/12, obtained commercially) was charged to a reaction flask equipped with stirrer, thermometer, condenser, and caustic scrubber. Approximately 280 parts of toluene was added and the mixture was heated to about 80° C. Over a period of 1 hour 61.7 parts of phosphorus pentasulfide was added batchwise at a temperature ranging from 80° C. to 85° C. The reaction mixture was held at 90° C. for 4 additional hours, at which time no further $H_2S$ evolution was observed. The reaction temperature was lowered to 60° C. and low vacuum (100 mm of Hg) was applied for 15 minutes. The reaction solution was filtered hot through paper to remove the small amount ($<0.5$ part) of unreacted phosphorus pentasulfide. The resulting clear, orange solution was used for subsequent reactions.

EXAMPLE 3

N,N-dimethyl-N-oleylamine Salt of phosphosulfurized N,N-(bis-2-hydroxyethyl) oleamide Approximately 85 parts of phosphosulfurized N,N-(bis-2-hydroxyethyl)oleamide, prepared as described in Example 2, was dissolved in 200 cc isopropanol solvent. 95.2 parts of N,N-dimethyl-N-oleyl-amine were added dropwise to the stirred reaction solution until the reaction pH was 9.2. The solution was refluxed at 82° C. for 3 hours. The solvent was removed by vacuum distillation and the product was filtered through diatomaceous earth to yield a clear, yellow fluid.

EXAMPLE 4

Synthesis of oleylamine salt of phosphosulfurized N,N-(bis-2-hydroxyethyl)oleamide Approximately 50 parts of phosphosulfurized N,N-(bis-2-hydroxyethyl) oleamide in 19 parts of toluene and 26.5 parts of oleylamine were refluxed for 3 hours in 22 parts of isopropanol. The solvents were removed by vacuum distillation, and the residue was filtered through diatomaceous earth to yield a viscous, orange liquid.

EXAMPLE 5

Synthesis of N-oleyl-1,3-propylene diamine salt of phosphosulfurized N,N-(bis-2-hydroxyethyl)oleamide Approximately 50 parts of phosphosulfurized N,N-(bis-2-hydroxyethyl) oleamide in 19 parts of toluene and 12.4 parts of N-oleyl-1,3-propylene diamine were refluxed for 3 hours in 26 parts of isopropanol. The solvents were removed by vacuum distillation, and the residue was filtered through diatomaceous earth to yield a viscous, orange liquid.

EVALUATION OF THE COMPOUNDS

The compounds were evaluated in a low velocity friction apparatus (LVFA) in a fully formulated 5W-20 oil containing an additive package including antioxidant, dispersant and detergent and inhibitors. The friction reducing compound was 1-5% of the total weight of oil. Base oil had the following general characteristics:

| Kinematic Viscosity | @ 100° C. | 6.8cs |
|---|---|---|
|  | @ 40° C. | 36.9cs |
| Viscosity Index | 143 | |

Description

The Low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque armstrain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12-13 ml. of test lubricants are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 min. at 250° F., 240 psi, and 40 fpm sliding speed. Afterward, measurements of $U_k$ vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis of comparison. The results were obtained at 250° F. and 500 psi.

TABLE 1

| | Friction Characteristics | | |
|---|---|---|---|
| | Additive Conc., | Reduction or % Change in Coefficient of Friction | |
| Example No. | Wt. % | 5 Ft./Min. | 30 Ft./Min. |
| 3 | 4 | 20 | 22 |
| 4 | 4 | 20 | 20 |
| 5 | 4 | 17 | 16 |
| Base Oil | 0 | 0$^{(a)}$ | 0$^{(a)}$ |

$^{(a)}$Value for base fluid assigned as zero point.

The products were also evaluated for oxidation stability. In most cases improvements in oxidative stability over the base oil were observed. Basically the test lubricant is subjected to a stream of air which is bubbled through at the rate of 5 liters per hour at 325° F. for 40 hours. Present in the composition are samples of metals commonly used in engine construction, namely iron, copper, aluminum and lead. See U.S. Pat. No. 3,682,980, incorporated herein by reference, for further details of the test. Improvement in viscosity increase and neutralization number show effective control. See the results in Table 2.

TABLE 2

| | Catalytic Oxidation Test | | |
|---|---|---|---|
| Example No. | Additive Conc., Wt., % | % Increase in Viscosity of Oxidized Oil Using KV @ 210° F. | Neut. Number NN |
| Base Oil, 0% additive 200" Solvent Paraffinic Neutral Lubricating Oil. | — | 67 | 3.62 |
| 3 | 1 | 15 | 1.92 |
| | 3 | 7 | 1.93 |
| 4 | 1 | 14 | 2.4 |
| | 3 | 19 | 2.03 |
| 5 | 1 | 17 | 2.52 |
| | 3 | 5 | 1.88 |

Also, copper strip corrosion tests were run in accordance with ASTM D130-80, the results of which are shown in Table 3.

TABLE 3

| | Copper Strip Corrosivity Characteristics | | |
|---|---|---|---|
| Example No. | Conc. in 200" SPN | ASTM D130-80 250° F. 3 Hrs. | ASTM D130-80 210° F. 6 Hrs. |
| Example 3 N,N—dimethyl-N— oleylamine salt of phosphosulfurized N,N— (bis-2-hydroxyethyl) oleamide | 1 | 2B | 1A |
| | 3 | 1A | 1A |
| Example 4 Oleylamine salt of phosphosulfurized N,N—(bis-2-hydroxy- ethyl)oleamide | 1 | 2C | 1A |
| | 3 | 4B | 3B |
| Example 5 N—oleyl-1,3- propylene diamine salt of phospho- sulfurized N,N—(bis- 2-hydroxyethyl)oleamide | 1 | 2C | 1A |
| | 3 | 3B | 3B |

We claim:
1. A reaction product made by (1) reacting, at from about 50° C. to about 140° C., a phosphorus polysulfide with a hydroxy aliphatic hydrocarbylamide of the formula:

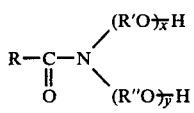

wherein R is a hydrocarbyl group containing 6 to 30 carbon atoms, R' and R" are aliphatic groups containing 1 to 6 carbon atoms and x and y are each 1 to 7, using from about 2 to about 12 moles of the hydrocarbylamide per mole of polysulfide, followed by (2) reacting (1), at from about 50° C. to about 120° C., with a stoichiometric amount of a nitrogen-containing compound.

2. The product of claim 1 wherein R is alkyl, alkenyl, cycloalkyl, cycloalkenyl, aralkyl or alkaryl.

3. The product of claims 1 or 2 wherein R' and R" are selected from the group consisting of methyl, ethyl, propyl, isopropyl, butyl, secondary butyl, isobutyl, pentyl, isopentyl and hexyl groups.

4. The product of claim 3 wherein the phosphorus polysulfide is phosphorus pentasulfide.

5. The product of claim 4 wherein the nitrogen-containing compound is an aliphatic or aromatic amine having 6 to 30 carbon atoms.

6. The product of claim 5 wherein the amine is selected from the group consisting of cyclohexylamine, hexylamine, octylamine, nonylamine, oleylamine, stearylamine, cocoamine, N-coco-1,3-propylenediamine, N-oleyl-1,3-propylenediamine, N-methyl-N-oleylamine, N-methyl-N-cocoamine, N,N-dimethyl-N-oleylamine and N,N-dimethyl-N-cocoamine.

7. The product of claim 1 wherein R is oleyl, R' and R" are ethyl, x is 1, y is 1, the phosphorus polysulfide is phosphorus pentasulfide and the nitrogen-containing compound is N,N-dimethyl-N-oleylamine.

8. The product of claim 1 wherein R is oleyl, R' and R" ethyl, x is 1, y is 1, the phosphorus polysulfide is phosphorus pentasulfide and the nitrogen-containing compound is oleylamine.

9. The product of claim 1 wherein R is oleyl, R' and R" are ethyl, x is 1, y is 1, the phosphorus polysulfide is phosphorus pentasulfide and the nitrogen-containing compound is N-oleyl-1,3-propylenediamine.

10. A lubricant composition comprising a major amount of a lubricant and a friction reducing amount of the reaction product of claim 1.

11. The composition of claim 8 wherein R is alkyl, alkenyl, cycloalkyl, cycloalkenyl, aralkyl or alkaryl.

12. The composition of claims 10 or 11 wherein R' and R" are selected from the group consisting of methyl ethyl, propyl, isopropyl, butyl, secondary butyl, isobutyl, pentyl, isopentyl and hexyl groups.

13. The composition of claim 12 wherein the phosphorus polysulfide is phosphorus pentasulfide.

14. The composition of claim 13 wherein the nitrogen-containing compound is an aliphatic or aromatic amine having 6 to 30 carbon atoms.

15. The composition of claim 14 wherein the amine is selected from the group consisting of cyclohexylamine, hexylamine, octylamine, nonylamine, oleylamine, stearylamine, cocoamine, N-coco-1,3-propylenediamine, N-oleyl-1,3-propylenediamine, N-methyl-N-oleylamine, N-methyl-N-cocoamine, N,N-dimethyl-N-oleylamine and N,N-dimethyl-N-cocoamine.

16. The composition of claim 10 wherein in said product R is oleyl, R' and R" are ethyl, x is 1, y is 1, the phosphorus polysulfide is phosphorus pentasulfide and the nitrogen-containing compound is N,N-dimethyl-N-oleylamine.

17. The composition of claim 10 wherein in said product R is oleyl, R' and R" are ethyl, x is 1, y is 1, the phosphorus polysulfide is phosphorus pentasulfide and the nitrogen-containing compound is oleylamine.

18. The composition of claim 10 wherein in said product R is oleyl, R' and R" are ethyl, x is 1, y is 1, the phosphorus polysulfide is phosphorus pentasulfide and the nitrogen-containing compound is N-oleyl-1,3-propylenediamine.

19. The composition of claim 10 wherein the lubricant is a lubricating oil.

20. The composition of claim 10 wherein the lubricant is a grease.

21. The composition of claim 19 wherein said lubricating oil is a mineral oil.

22. The composition of claim 19 wherein said lubricating oil is a synthetic oil.

23. The composition of claim 19 wherein said lubricating oil is a mixture of mineral and synthetic oils.

* * * * *